(12) United States Patent
Holland

(10) Patent No.: US 6,235,487 B1
(45) Date of Patent: *May 22, 2001

(54) METHOD OF DIAGNOSING CROHN'S DISEASE

(76) Inventor: Stephen Holland, 1108 W. Nassau Dr., Peoria, IL (US) 61615-1379

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/117,061
(22) PCT Filed: Sep. 30, 1996
(86) PCT No.: PCT/US96/15629
§ 371 Date: May 22, 1998
§ 102(e) Date: May 22, 1998
(87) PCT Pub. No.: WO97/16730
PCT Pub. Date: May 9, 1997

Related U.S. Application Data

(60) Provisional application No. 60/007,218, filed on Nov. 3, 1995.

(51) Int. Cl.[7] .................................................. G01N 33/53
(52) U.S. Cl. ........................... 435/7.1; 435/7.2; 435/7.24; 435/7.32; 435/7.34
(58) Field of Search ............................ 435/7.1, 7.2, 7.34, 435/7.24, 6, 7.32

(56) References Cited

U.S. PATENT DOCUMENTS

| | | |
|---|---|---|
| 3,746,624 | 7/1973 | Hoerman et al. . |
| 3,902,969 | 9/1975 | Gold . |
| 4,166,767 | 9/1979 | Kurooka et al. . |
| 4,250,262 | 2/1981 | Taubman et al. . |
| 4,324,782 | 4/1982 | Beck . |
| 4,692,407 | 9/1987 | Jordan et al. . |
| 4,693,968 | 9/1987 | Kitagawa . |
| 4,789,735 | 12/1988 | Frank et al. . |
| 4,992,365 * | 2/1991 | Hyman . |
| 5,079,141 | 1/1992 | Niskanen et al. . |
| 5,281,524 | 1/1994 | Horikoshi et al. . |
| 5,334,503 | 8/1994 | Snyder et al. . |

FOREIGN PATENT DOCUMENTS

WO 90/00201  12/1990  (WO) .

OTHER PUBLICATIONS

Klasen L.S. (Jun. 1994) Clin Immunology and Immunopathology 71(3) 303–308.*
Sundh et al (Nov. 1993) Oral Surg Oral Med Oral Pathol 76:564–569.*
Meurman et al (May 1994) Oral Surg Oral Med Oral Pathol 77:465–468.*
Merrian Webster's Collegiate Dictionary, Tenth Edition Merrian–Webster Inc. SpringField, Mass USA p. 319, 1996.*
Berghouse, L. et al., "Comparison between the bacterial and oligosaccharide content of ileostomy effluent in subjects taking diets rich in refined or unrefined carbohydrate," *Gut* 25: 1071–1077 (Oct. 1984).
Cromartie, W.J. et al., "Arthritis in Rats After Systemic Injection of Streptococcal Cells or Cell Walls," *J. Exp. Med.* 146:1585–1602 (Dec. 1977).
Klasen, I.S. et al., "The Presence of Peptidoglycan–Polysaccharide Complexes in the Bowel Wall and the Cellular Response to These Complexes in Crohn's Disease," *Clin. Imm. Immun.* 71:303–308 (Jun. 1994).
McCarty, M. and Lancefield, R., "Variation in the Group–Specific Carbohydrate of Group A Streprococci," *J. Exp. Med.* 102:11–28 (1955).
Meurman, J.H. et al., "Gingival and dental status, salivary acidogenic bacteria, and yeast counts of patients with active or inactive Crohn's disease," *Oral Medicine* 77:465–468 (May 1994).
Stimpson, S.A. et al., "Arthropathic Properties of Cell Wall Polymers from Normal Flora Bacteria," *Infect. Imm.* 51:240–249 (Jan. 1986).
Sundh, B. et al., "Salivary antimicrobial proteins in patients with Crohn's disease," *Oral Medicine* 76:564–569 (Nov. 1993).

\* cited by examiner

*Primary Examiner*—David Saunders
*Assistant Examiner*—Amy DeCloux
(74) *Attorney, Agent, or Firm*—Sterne, Kessler, Goldstein & Fox P.L.L.C.

(57) ABSTRACT

A method of diagnosing Crohn's disease is described. The method assays for the presence of an immune response to *S. mutans* antigens in a sample from a patient.

10 Claims, 2 Drawing Sheets

METHOD OF DIAGNOSING CROHN'S DISEASE

CROSS REFERENCES TO RELATED APPLICATIONS

This application is the U.S. National Phase of PCT/US96/15629, internationally filed Sep. 30, 1996, which claims the benefit of U.S. Application Ser. No. 60/007.218, filed Nov. 3, 1995.

FIELD OF THE INVENTION

The present invention relates generally to methods to diagnose inflammatory conditions triggered by the presence of certain bacteria. Particularly, the invention is directed to an assay for the detection of a patient's immune response against certain bacteria. The presence of this immune response is useful in diagnosing certain inflammatory diseases such as Crohn's disease.

BACKGROUND OF THE INVENTION

Crohn's disease is an inflammatory disease of the gastrointestinal tract, most often affecting the ileum and colon, but which may affect any part of the digestive tract from the mouth to the anus. The disease manifestations usually are isolated to the digestive tract, but other manifestations such as inflammation of skin structures, the eyes, and the joints have been well described. The disease is known to have spontaneous exacerbations and remissions.

The cause of Crohn's disease is not known. One of the oldest theories is that Crohn's disease is caused by infection by or immune response against certain bacterial species. That theory is based on the similarity of the microscopic appearance of diseased tissue in Crohn's disease to the microscopic appearance of diseased tissue in mycobacterial disease such as tuberculosis. Further studies have not conclusively shown that mycobacterial species are causal in Crohn's disease. It is generally thought that Crohn's disease is an autoimmune disease, but that there may be an important role for some bacteria, though what that role might be is unknown.

The type of inflammatory response in Crohn's disease is a granulomatous response. It is known that the bacterial products from the cell walls of bacteria can cause a granulomatous response in susceptible animals such as certain strains of rat. Other facts known about Crohn's disease are that it runs in families, is rare in infants, patients with Crohn's disease eat more sugar, patients treated with a sucrose free diet have less complications of Crohn's disease, patients with exacerbations of their Crohn's symptoms often have resolution of the symptoms when placed on formula diets (all of which are sucrose free), Crohn's seems to have lesions in the gut in areas of stasis, many patients with Crohn's disease do well when treated with oral antibiotics, and diversion of the intestinal stream by surgical intervention leads to resolution of disease in the excluded segment, only to see recurrence when the intestine is reattached.

*S. mutans* is a mouth-associated organism that produces an enzyme known as glucosyltransferase. Glucosyltransferase polymerizes sucrose to create a polymer that aids in adhering *S. mutans* to teeth and in protecting the organism from the host. *S. mutans* sheds bacterial components into the digestive tract. Some components that are shed are the end products of *S. mutans* metabolic pathways; others due to normal cell constituent turnover and death.

Some reports in the medical literature have looked at the presence of *S. mutans* in patients with Crohn's disease. Meurman, J. K. et. aL, *Oral Surg. Oral Med Oral Pathol* 77:465–468 (1994) reported that patients with active Crohn's disease had higher counts of *S. mutans* than patients with inactive disease. Their study did not make any measures of immune response. They hypothesized that increased *S. mutans* counts were secondary to the fact that their patients had also increased their sucrose intake because sucrose "is more digestible and causes less gastrointestinal symptoms than a fat-containing diet" in Crohn's disease patients.

Sundh, B. et. al, *Oral Surg. Oral Med. Oral Pathol* 76:564–569 (1993) also studied patients with Crohn's disease, and reported average *S. mutans* counts as well as general measures of immunity in patients and controls. Salivary IgA antibody levels were measured, but they did not test whether the antibody would recognize *S. mutans*, and only IgA antibodies were measured. Their report of the average number of *S. mutans* in patients is not a comparable statistic to the number of patients with high or low counts as reported by Meurman. Their study did not make any measures of specific immune response against *S. mutans*.

Berghouse et. al. *Gut* 25:1071–1077 (1984) reported that not all sucrose ingested by patients with an ileostomy could be accounted for when the output of the ileal output was measured for sucrose. The assay tested for sucrose monomers and small molecular weight sucrose polymers. The study did not show a difference in sucrose concentration between Crohn's disease patients and otherwise normal ileostomy patients.

Clinicians diagnose Crohn's disease by history, physical examination, x-ray studies with or without barium contrast material within the digestive tract, and colonoscopy or upper endoscopy. In early Crohn's disease, however, there may be little in the way of narrowing of the terminal ileum visible on x-ray studies.

There are general tests that reflect inflammation, such as erythrocyte sedimentation rate, C reactive protein, and orosomucoids, but there are no specific tests for Crohn's disease. A blood test for Crohn's disease would be of considerable utility, allowing confirmation of the diagnosis in the frequent case of trying to diagnose early Crohn's disease, where the absence of specific findings on x-ray and endoscopic studies may lead to the diagnosis of irritable bowel syndrome or nonspecific colitis. Depending on the characteristics of the test, a number of useful results such as prediction of clinical course, need for surgery, establishing risk of Crohn's disease in family members, or other important results may be obtained. A test that could be performed on surgical specimens removed from patients which would confirm the diagnosis of Crohn's disease would also be useful because often the characteristic histologic findings for Crohn's disease are absent in surgical specimens.

SUMMARY OF THE INVENTION

Recognizing the need for a simple assay for Crohn's disease, the inventor investigated the relationship between Crohn's disease and immunological reactivity in such patients. These studies have resulted in the development of a simple assay for Crohn's disease that detects the patient's immunological response to *S. mutans* antigens.

DETAILED DESCRIPTION OF THE PREFERRED EMBODIMENTS

Figure 1:
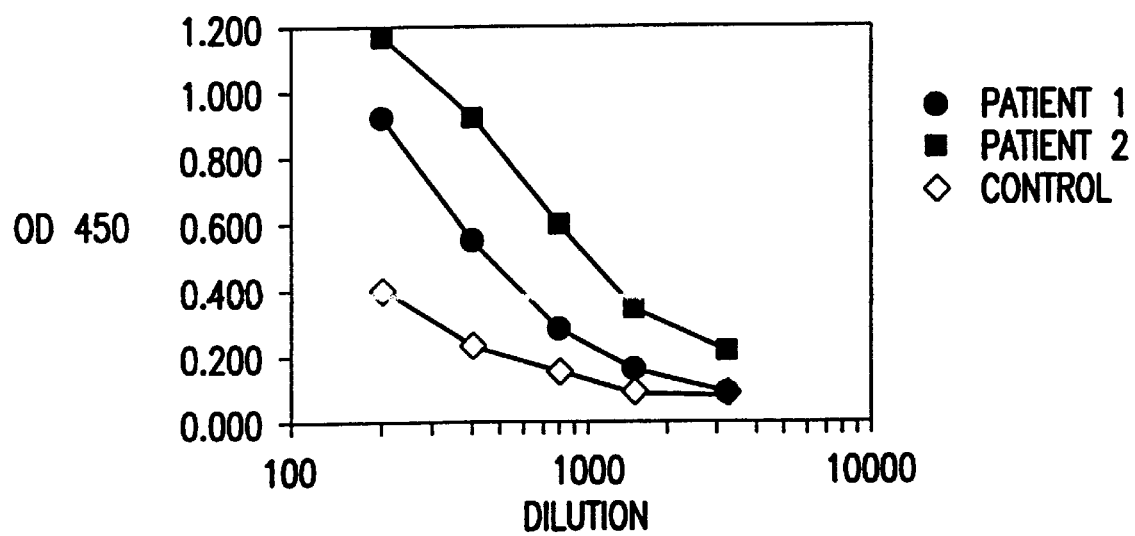
FIG. 1 shows the titration curves for the ELISA assays.

The invention lies in the discovery that a diagnosis or prognosis for Crohn's disease is correlated with the development of, or stimulation of, an immune response to *S. mutans* in a patient. It has been discovered that while *S. mutans* is a ubiquitous organism found in the mouth of people worldwide, an immunological response to *S. mutans* can be detected in those individuals who are disposed to developing or exacerbating symptoms of Crohn's disease. Thus, the invention provides methods for diagnosing Crohn's disease in humans and animals based upon the previously unrecognized and unsuspected causal role that it has been discovered that *S. mutans* plays in the pathogenesis of Crohn's disease. The invention is useful in both human medical and veterinary settings. Further, when applied to animal models, the invention also provides for the evaluation of such animal models of Crohn's disease.

The invention provides diagnostic assays based on the interaction between a component of the patient's immune system and an antigen or antigens from *S. mutans*, or products of metabolism of *S. mutans*. Preferred embodiments of the method of the invention include:

1. The diagnosis of Crohn's disease by immunologic assays using antigens from *S. mutans* and samples from subjects in need of such diagnosis, to measure antibodies that bind to *S. mutans* in such samples, the presence of such antibodies being used to diagnose Crohn's disease.

2. The use of antibodies that bind to antigens from *S. mutans* in immunologic assays to determine the presence of antigens derived from *S. mutans*, where the presence of *S. mutans* antigens is used to diagnose Crohn's disease. Thus, the method of the invention includes methods that detect antigens from *S. mutans* in a sample by binding such antigens, for example, to a matrix, in a non-specific manner or in a specific manner, for example, with the use of *S. mutans* specific antibodies, and then detecting such non-specific or specific binding by use ot *S. mutans* specific antibodies. In the case where antigens of *S. mutans* are already in a solid matrix, such as, for example, biopsy specimens embedded in paraffin, methods that detect the binding of antibodies specific for *S. mutans* to the immobilized antigens can be used.

3. The use of immunologic assays using antigens from *S. mutans* to determine if there is an effect upon cells from patients or animals isolated from peripheral blood, lymph nodes, or other tissues. Thus, for example, the invention comprises methods that detect an effect of antigens from *S. mutans* upon, for example, proliferation of cells in samples, or that detects an effect upon cytokines released by cells in samples.

The above three examples of methods are not the only methods by which one skilled in the arts of medicine, microbiology, and immunology may use the invention. Any method that allows determination of an interaction of the immune system with *S. mutans* or allows determination of the presence of antigens from *S. mutans* in a sample is useful in the method of the invention.

According to the method of the invention, a diagnosis of Crohn's disease in a patient suspected of having such disease, or an evaluation of the severity or progression of Crohn's disease in a patient already diagnosed as having the same, is made by detecting an immune response against *S. mutans* in a sample from the patient in need of such diagnosis. When it is desired to detect antibodies, generally and preferably, antibodies in the patient's sample are detected that bind to antigens from *S. mutans*. The detection of antibodies that bind to antigens from *S. mutans* can be performed by directly detecting the binding of such antibodies to antigens from *S. mutans*. Alternatively, the detection of antibodies that bind to antigens from *S. mutans* can be performed by indirectly detecting the binding of such antibodies to antigens from *S. mutans*. By directly detecting the binding is meant that the label or indicator, the presence of which is ultimately measured, is on either the antibodies to *S. mutans* or the *S. mutans* antigen. By indirectly detecting the binding is meant that the label or indicator, the presence of which is ultimately measured, is not present on either the antibodies to *S. mutans* or the *S. mutans* antigen. Alternatively, the diagnosis of Crohn's disease according to the invention may be made using a cellular assay that detects an effect of antigens from *S. mutans* upon a cellular parameter, such as, for example, proliferation of cells.

In the art of immunology, the term antigen means any substance that induces a specific immune response against itself. While classically the term was used in the context of antibody responses, the term now encompasses responses in cellular and humoral (serum) immune responses. Substances may also affect the immune system by stimulating the immune response to another antigen. This is called an adjuvant effect. As used herein, a substance from *S. mutans* acting as such an adjuvant is included under the term antigen.

By "antigen from *S. mutans*" or "antigens from *S. mutans*" is meant any antigen, natural or synthetic, alone or in combination with other antigens, that is capable of eliciting an immune response useful for the detection of *S. mutans*. Such antigens can be from any strain of the bacterial species *S. mutans* (including strains previously classified as *S. mutans* but now renamed *S. rattus*, *S. cricetus*, and *S. sobrinus*, all considered as *S. mutans* for the purposes of this invention).

The term "antibody" is intended to be synonymous with "immunoglobulin." As used herein, the term "antibody" is meant to include both the native antibody, and biologically active derivatives of antibodies, such as, for example, Fab', F(ab')$_2$ or Fv as well as single-domain and single-chain antibodies. A biologically active derivative of an antibody retains the ability to bind antigen.

By "antibody against *S. mutans*" is meant an antibody or antibody mixture, derived from sera and/or biochemical techniques such as monoclonal antibody technology, biochemical synthesis, or other techniques, that binds to an antigen or antigens of *S. mutans*, as defined above. By "*S. mutans* antibody" is meant an antibody against *S. mutans*.

By "react with" an antigen is meant that the antibody possesses an affinity for the antigen that results in the formation of a non-covalent complex between the antibody and antigen.

The antigens useful in the methods of the invention are those antigens from *S. mutans* against which an immune response can be detected. The antibodies to *S. mutans* in the patient's sample, and especially in a blood or tissue sample, can be detected using *S. mutans* antigens in immunoassays wherein the antigen can be utilized in liquid phase or bound to a solid phase carrier. In addition, the *S. mutans* antigen can be detectably labeled in various ways for use in immunoassays for *S. mutans* antibody. The preferred immunoassays for detecting *S. mutans* antibodies using the methods of this invention include radioimmuno-assays, enzyme-linked immunosorbent assays (ELISA), or other assays known in the art, such as immunofluorescent assays, chemiluminescent assays, or bioluminescent assays. The preferred immunoassay for detecting effects of antigens from *S. mutans* upon immune cells is a tritiated thymidine uptake proliferation assay.

Radioactive isotopes which are particularly useful in assays are $^3$H, $^{125}$I, $^{131}$I, $^{32}$P $^{35}$S, $^{14}$C, $^{51}$Cr, $^{36}$Cl, $^{57}$Co, $^{58}$Co, $^{59}$Fe, $^{75}$Se, and $^{152}$Eu.

While radiolabeling represents one embodiment, alternatively, the *S. mutans* antigens or antibodies thereto may also be labeled using fluorescent labels, enzyme labels, free radical labels, avidin-biotin labels, or bacteriophage labels, using techniques known to the art.

Typical fluorescent labels include fluorescein isothiocyanate, rhodamine, dichlorotriazinylamino fluorescein, Texas Red, XRITC, morpholinorhodamine isothiocyanate, phycoerythrin, phycocyanin, allophycocyanin, o-phthaldehyde, and fluorescamine.

Typical chemiluminescent compounds include luminol, isoluminol, aromatic acridinium esters, imidazoles, acridinium salts, and the oxalate esters. Typical bioluminescent compounds include luciferin, luciferase, and aequorin.

Typical enzymes include alkaline phosphatase, β-galactosidase, glucose-6-phosphate dehydrogenase, maleate dehydrogenase, glucose oxidase, urease and peroxidase.

Two principal types of enzyme assays are enzyme-linked immunosorbent assay (ELISA) and the homogeneous enzyme immunoassay, also known as enzyme-multiplied immunoassay (EMIT) (Syva Corp.). The EMIT system depends on deactivation of the enzyme in the tracer-antibody complex; the activity can thus be measured without the need for a separation step.

The immunoassays useful in the method of the invention also include latex agglutination assays, immunometric assays and competitive assays.

Latex agglutination assays have been described in Beltz, G. A. et al., in *Molecular Probes: Techniques and Medical Applications*, A. Albertini et al., eds., Raven Press, New York, 1989, incorporated herein by reference. In the latex agglutination assay, antigen or antigens from *S. mutans* is immobilized on latex particles. A drop of the latex particles is added to an appropriate dilution of the serum to be tested and mixed by gentle rocking of the card. With samples lacking antibodies to *S. mutans*, the latex particles remain in suspension and retain a smooth, milky appearance. However, if antibodies reactive with the *S. mutans* antigen are present, the latex particles clump into visibly detectable aggregates. The latex agglutination assay is especially suitable for small volume users, emergency situations, and areas lacking the sophisticated laboratory equipment and supplies needed for immunometric assays.

An agglutination assay can also be used to detect *S. mutans* antibodies wherein the desired antigen is immobilized on a suitable particle other than latex beads, for example, on gelatin, red blood cells, nylon, liposomes, gold particles, etc. The presence of antibodies in the same causes agglutination, similar to that of a precipitation reaction, which can then be detected by such techniques as nephelometry, turbidity, infrared spectrometry, visual inspection, colorimetry, and the like.

Immunometric assays include forward sandwich, reverse sandwich immunoassays and simultaneous assay. Each of these terms is well-understood by those skilled in the art. In these assays, the antigen is bound to a solid-phase carrier and antibodies, generally anti-IgG antibodies, are detectably labeled.

In a forward sandwich immunoassay, a sample suspected of containing antibodies against *S. mutans* is first incubated with a solid-phase immunoadsorbent to which an appropriate *S. mutans* antigen has been bound. Incubation is continued for a period of time sufficient to allow the antibodies in the sample to bind to the immobilized *S. mutans* antigen(s). After the first incubation, the solid-phase immunoadsorbent is separated from the incubation mixture and washed to remove interfering substances which also may be present in the sample. Solid-phase immunoadsorbent-containing antibodies bound to the immobilized antigen are subsequently incubated for a second time with soluble labeled antibody cross-reactive with a different domain on the antibody to be detected. After the second incubation, another wash is performed to remove unbound labeled antibody from the solid-phase immunoadsorbent and to remove non-specifically bound labeled antibody. Labeled antibody bound to the solid-phase immunoadsorbent is then detected and the amount of labeled antibody detected serves as a direct measure of the amount of antibodies present in the original sample. Alternatively, labeled antibody which is not associated with the immunoadsorbent complex can also be detected, in which case the measure is in inverse proportion to the amount of antigen present in the sample. Forward sandwich assays are described, for example, in U.S. Pat. Nos. 3,867,517; 4,012,294; and 4,376,110.

In a reverse sandwich assay, the sample suspected of containing test antibodies against *S. mutans* is initially incubated with labeled anti-antibody, after which the solid-phase immunoadsorbent containing immobilized antigen cross-reactive with a different domain on the test antibody is added thereto, and a second incubation is carried out. The initial washing step required by a forward sandwich assay is not required, although a wash is performed after the second incubation. Reverse sandwich assays have been described, for example, in U.S. Pat. Nos. 4,098,876 and 4,376,110.

In a simultaneous sandwich assay, the sample, the immunoadsorbent having immobilized antigen thereon and labeled soluble antibody specific to a different domain of the test antibody are incubated simultaneously in one incubation step. The simultaneous assay requires only a single incubation and does not require washing steps. The use of a simultaneous assay is a very helpful technique, providing ease of handling, homogeneity, reproducibility, linearity of the assays, and high precision. See U.S. Pat. No. 4,376,110 to David et al., incorporated by reference herein.

So-called delayed immunometric assays can also be utilized, as are, for example, described in Chu, U.S. Pat. No. 4,289,747, and Wolters, U.S. Pat. No. 4,343,896.

In each of the above assays, the antibody-containing sample, solid-phase immunoadsorbent with immobilized *S. mutans* antigen and labeled soluble antibody are incubated under conditions and for a period of time sufficient to allow the test antibodies to bind to the immobilized antigen and to the soluble antibodies. In general, it is desirable to provide incubation conditions sufficient to bind as much antibody as possible, since this maximizes the binding of labeled antibody to the solid phase, thereby increasing the signal. Of course, the specific concentrations of labeled antibodies and immobilized fragments, the temperature and time of incubation, as well as other such assay conditions, can be varied, depending upon various factors including the concentration of antibody in the sample, the nature of the sample, and the like. Those skilled in the art will be able to determine operative and optimal assay conditions for each determination by employing routine experimentation.

There are many solid-phase immunoadsorbents that have been employed and that can be used in the present invention. Well-known immnunoadsorbents include beads formed from glass, polystyrene, paper, polypropylene, dextran, nylon, and other material; tubes formed from or coated with such materials, and the like. The immobilized antigens may be covalently or physically bound to the solid-phase immunoadsorbent, by techniques such as covalent bonding via an amide or ester linkage or by adsorption. Those skilled in the art will know many other suitable carriers for binding antigens, or will be able to ascertain such, using routine experimentation.

General competitive binding assay techniques useful for the detection of minute amounts of desired substances are well-known in the art. See Chard, supra. Any of these competitive binding assay techniques can be used for the purposes of detecting *S. mutans* antibodies. In order to carry out a competitive binding assay, typically a radioimmunoassay (RIA), it is necessary to provide a binding molecule which has affinity for the label-containing antibody raised in response to an antigen, and for the *S. mutans* antibody to be tested as well. A small amount of the fluid or tissue sample containing an unknown quantity of *S. mutans* antibody is incubated in the presence of the raised labeled antibody and also a known amount of antibody-specific antigen.

Once the incubation of the test sample with the *S. mutans* antigen and tracer-containing antibody is complete, it is necessary to determine the distribution of the tracer-containing molecule between the free and bound (immunocomplexed) form. Usually, but not always, this requires that the bound fraction be physically separated from the free fraction. For example, the specific antigen can be bound to a plate. A variety of other techniques may be used for that purpose, each exploiting physical-chemical differences between the tracer-containing molecule in its free and bound form. The generally available methodologies have been described by Yalow, in *Pharmacol, Rev.* 28:161 (1973). These techniques include adsorption, precipitation, salting out techniques, organic solvents, electrophoretic separation, and the like. See Chard, supra, pp. 405–422.

As in the immunometric assays described above, the soluble antibody may be labeled with any detectable label, such as a radiolabel, a fluorescent label, an enzyme label, a free radical label, or a bacteriophage label. Most commonly, the label is a radiolabel or an enzyme label.

In the practice of this invention, the presence of antibodies to *S. mutans* or the bacteria or antigens of *S. mutans* itself may be detected in biological fluids and tissues. Any sample containing the unknown amount of antibodies to *S. mutans* or *S. mutans* antigens can be used. Normally, a sample is a liquid such as, for example, urine, saliva, tear drops, cerebrospinal fluid, blood, serum and the like, or a solid or semi-solid such as, for example, tissues, feces, and the like.

Antigens from *S. mutans* and optionally from a related species such as *S. pyogenes* (as described below) that are useful in the methods of the invention can be prepared from strains that are available from the ATCC. Such antigens can be obtained by making a cell wall preparation of *S. mutans* or *S. pyogenes*. One of ordinary skill in the art would understand that a cell wall preparation from *S. mutans* will have a number of proteins and other macromolecules and chemical structures present, all providing potential antigens that may be useful in the methods of the invention.

One preferred method of obtaining Streptococcal cell wall preparations is described by Stimpson et. al., *Infection and Immunity* 51:240–249 (1986)). Cell wall preparations of *S. pyogenes* and *S. mutans* are prepared with identical steps. All incubations are preferably performed at 37° C. in room air in covered, unstirred flasks. In a preferred embodiment, ten ml of Todd-Hewitt broth is inoculated with either *S. pyogenes*, preferably strain D58X or *S. mutans*, preferably strain MT8148. MT8148 is available from the Department of Dentistry of Osaka University, as described in U.S. Pat. No. 5,281,524. After 6 hours of incubation the culture is poured into 200 ml of Todd-Hewitt broth and incubated for 4 hours. 100 ml aliquots of the culture are then inoculated into 1.5 l flasks of Todd-Hewitt broth and are incubated overnight. Cells can be harvested, for example by centrifugation at 10000 g, washed, preferably three times, and killed, preferably heat killed at 80° C. for 30 minutes. Cells then are washed, preferably 3 times, ruptured, for example using a Braun homogenizer, washed, again preferably 3 times, extracted preferably 3 times in 2% SDS, incubated approximately 30 min. at preferably 56° C., washed preferably 7 times in water, and finally are lyopholized. Working stock suspensions are made up at, preferably, 20 mg/ml in PBS.

Another preferred method of obtaining Streptococcal cell wall preparations is described by Cromartie, et. al., *J. Exp. Med.* 146:1585–1602 (1977)). Cell wall preparations of *S. pyogenes* and *S. mutans* are prepared with identical steps. All incubations are preferably performed at 37° C. in room air in covered, unstirred flasks. Preferably, 10 ml of Todd-Hewitt broth is inoculated with either *S. pyogenes*, preferably strain D58X, or *S. mutans*, preferably strain MT8148. After an appropriate time, such as 6 hours of incubation, the culture is poured into an appropriate volume, for example 200 ml, of Todd-Hewitt broth and incubated for 4 hours. Preferably 100 ml aliquots of the culture are then inoculated into 1.5 l flasks of Todd-Hewitt broth and are incubated overnight. Preferably, cells are harvested by centrifugation at 10000 g, washed three times, and heat killed at 80° C. for 30 minutes. Then, preferably, cells are washed 3 times, are ruptured in homogenizer, such as, for example, a Braun homogenizer, are washed 3 times, are treated with 0.025% ribonuclease at 37° C. for 4 hours, are washed once, are treated with 0.025% trypsin at 37° C. for 4 hours, are washed 3 times in water, and finally are lyopholized. Working stock suspensions are preferably made up at 20 mg/ml in PBS.

Antibodies against *S. mutans* can be obtained by immunizing animals with a cell wall preparation of *S. mutans*. Any protocol which allows for the preparation of antibodies capable of binding to antigens from *S. mutans* is useful for the methods of the invention. Any antibody or fragment of antibody specific for an antigen or antigens from *S. mutans*, or cross reactive with antigen or antigens from *S. mutans* would be useful for the methods of these inventions.

The preparation of antisera in animals is a well-known technique (see, for example, Chard, supra, pp. 385–396; and *Antibodies, A Practical Handbook*, Vols. I and II, D. Catty, ed., IRL Press, Washington, D.C. (1988)). The choice of animal is usually determined by a balance between the facilities available and the likely requirements in terms of volume of the resultant antiserum. A large species such a goat, donkey and horse may be preferred, because of the larger volumes of serum readily obtained. However, it is also possible to use smaller species such as rabbit or guinea pig which often yield higher titer antisera. Usually, subcutaneous injection or injections of the antigenic material, such as a cell wall preparation, is used to stimulate production of antibody against *S. mutans* in the animal in which antibodies are to be raised. The detection of an antibody response in the animal may be carried out by testing the antisera with immunoassays such as an ELISA or another assay, for example, as described herein.

To one skilled in the art, it is well known that there is lot to lot variability of antibodies and antigen preparations.

Thus it is routine in such immunological protocols to perform a titration of the reagents to determine optimal working dilutions from lot to lot. Generally, initial dilutions of 1:1000 for antibody preparations can be used for antibodies.

The antigen preparations described herein, for example, the S. mutans antigen preparations, may be used to stimulate the production of antibodies against such antigens. In order to stimulate the production of antibody, the antigen may be coupled to a carrier protein such as bovine serum albumin, cholera toxin, or keyhole limpet hemocyanin (KLH), utilizing techniques well-known and commonly used in the art. Additionally, the antigens can be admixed with an immunologically inert or active carrier. Carriers which promote or induce immune responses, such as Freund's complete adjuvant, can be utilized.

Antibodies thus obtained may then be utilized in the various immunoassays to identify and quantitate the presence of S. mutans antigens, and thus Crohn's disease. Both polyclonal antibodies and monoclonal antibodies, produced by well-known techniques as described in Catty, supra, raised in response to the antigens of this invention can be utilized in immunoassays.

The preferred method for obtaining antibodies against S. mutans is that of McCarty and Lancefield (McCarty, M. and Lancefield, R. C., J. Exp. Med. 102:11–28 (1955)). Briefly, a cell wall preparation of S. mutans from 1.5 L of culture is prepared as above, and is suspended in 25 ml of a 1 mg/ml solution of pepsin in 0.01 M HCl at pH 2.0 for 2 hours, neutralized with 1 M NaOH, washed 3 times in phosphate buffered saline (PBS; 0.15 M phosphate-buffered saline, pH 7.2: NaCl 8.0 g/liter, KCl 0.2 g/liter, $Na_2HPO_4$ 1.15 g/l and $KH_2PO_4$ 0.2 g/l), and finally suspended in 50 ml of 0.9% NaCi (saline). New Zealand White Rabbits are injected intravenously with 0.5 ml of suspension for the first three days of the first week, followed by 1.0 mnl for the first three days of each successive week for the following 3 weeks. After the fourth week serum is harvested from the rabbits.

Labeled antibodies specific for rabbit antibodies, as well as labeled antibodies specific for the various classes and subclasses of human antibodies may be prepared using methods known in the art or commercially purchased from a number of sources. Fab fragments of antibodies are also easily prepared using protocols well known to those with ordinary skill in the art. References for methods useful to the invention include Monoclonal Antibodies: Principles and Practice, Goding, Academic Press, Boston, 1986.

Any protocol which allows for the detection of antibodies specific for antigens from S. mutans is useful for the methods of the invention. Especially, any ELISA, SDS-polyacrylamide gel electrophoresis (SDS-PAGE), or Western Blot protocol that will detect binding of antibodies to antigens from S. mutans is useful for the methods of the invention. References that review the methods useful in the invention include Gel electrophoresis of proteins, a practical approach, Hames&Rickwood, eds., IRL press, Washington DC, 1981; and Practical Immunology, Hudson&Hay, Blackwell Scientific Publications, Boston, 1989.

In one embodiment, antibodies in a sample, preferably serum, that bind antigens from S. mutans are detected by running an ELISA using antigens from S. mutans to initially coat the ELISA plate and then adding the patient's sample that is to be tested. In the case where the sample is a fluid, the sample is used as is or is diluted, preferably in a buffer. In the case where the sample is a tissue or other solid specimen, the sample is preferably first homogenized and then any antibody that is present is extracted, preferably by centrifugation of the homogenate. This results in a supernatant fraction that is then tested and used as the sample. Methods for such homogenization and separation are well known in the art.

A preferred optional step applicable to any of the immunoassays which measure the amount of antibodies against S. mutans in a specimen is to adsorb-out cross reactive antibodies in the patient sample with another Streptococcal species. S. mutans shares a number of antigens with other members of the genus Streptococcus. In the course of usual health, a patient may develop a number of antibodies that will react against those antigens, and thus produce a positive result in an immune assay using S. mutans antigens. By first contacting a patient sample with an antigen preparation from another Streptococcal species, for example, S. pyogenes, the antibodies in the patient sample that react with the S. pyogenes antigens will be bound and may thus be removed from the patient sample. Subsequently, proceeding with the ELISA described above, only antigens unique to S. mutans will be detected. To one of ordinary skill in the art, this is referred to as adsorbing out cross reactive antibodies. To one of ordinary skill in the art it is obvious that any one of a number of streptococcal species could be used for preparing adsorbing antigen preparations.

In another embodiment, the presence of antibodies specific for S. mutans is revealed by subjecting S. mutans antigen or antigens to electrophoretic separation such as SDS-PAGE, followed by a Western blot transfer to a membrane. The membrane is then contacted with a sample from a patient, preferably serum diluted in buffer, that may have antibodies that bind to the antigens on the membrane. The bound antibodies are then detected. With this method, the preferred optional step of preadsorbing the patient sample may still be used, but with the antigens present on the blot arranged in order of molecular weight, the necessity of reducing the binding to cross reactive antigens is reduced by the fact of the spatial separation of the antigens on the membrane. To one of ordinary skill in the art it is obvious that any one of a number of chromatographic methods, transfer methods, and protocols for detecting antibodies bound to the separated antigens would be useful for the methods of the invention, and achieve the same end, the identification of Antibodies to S. mutans in the patient's sample.

The presence of antigens from S. mutans in samples can be detected by any process that reveals the presence of the antigens. For example, activity measurements of enzymes of S. mutans or immunochemical assays may be used. In the preferred embodiment for patient fluids, an ELISA with a first layer of antibody or antibodies specific for S. mutans, and a sample of a patient body fluid, preferably serum, is used. In the preferred embodiment for tissue samples, an immunohistochemistry method is performed, using antibodies specific for S. mutans.

The presence of antibodies specific for S. mutans in tissues can be detected by any process that reveals the presence of the specific antibodies. In the preferred embodiment, immunohistochemistry is performed using S. mutans antigens, preferably from a cell wall preparation, and an antibody that binds to antigens from S. mutans, preferably immune rabbit serum, as well as a detection system for bound rabbit antibodies, to detect binding of the S. mutans antigens by antibodies in the tissue sections.

Immunohistochemistry techniques are known to one skilled in the art. References to techniques include Hsu, et. al. J Histochem and Cytochem, 29:577–580 (1981). To those skilled in the art it is well known that lot to lot variability of reagents exist and small differences in conditions can affect the performance of assays. Thus it is obvious that reagents require titration and changes in protocols are required to accommodate differences in reagents and conditions of assays.

The effect upon activation or suppression of cells from a patient by antigens from *S. mutans* can be detected by any process that reveals the presence of the effect upon activation or suppression. In the preferred embodiment, white blood cells from some fluid or tissue, preferably whole blood, are isolated, placed in tissue culture in RPMI-1640 culture medium with additives, and antigen from *S. mutans* is added to the culture. After a time, cellular proliferation is measured by tritiated thymidine incorporation assay. To one of ordinary skill in the art, it is obvious that a number of changes can be made in this protocol including isolating cellular fractionations by means of cell density, surface proteins or other means, labeling methods, time course of mitogenisis, cell concentrations, antigen concentration, or other aspects of the assay.

In all the immune assays which measure or detect antibodies again *S. mutans*, it is possible to determine whether any antibody against *S. mutans* is present, as well as to determine what class and subclass of antibody is binding. This can be done by using commercially available detecting antibodies that are specific for the classes and subclasses of antibody. The class and subclass of antibody specific for *S. mutans* in the sample may provide important diagnostic information, including but not limited to the acuteness of the immune response, or whether the response represents immune modulation by Th1 or Th2 type T cells of the patient whose specimen is being assayed.

In addition, the materials for use in the assays of the invention are ideally suited for preparation of a kit. Such a kit may comprise a carrier means being compartmentalized to receive in close confinement one or more container means such as vials, test tubes, and the like. Each of said container means comprises one of the separate elements to be used in the method.

For example, one of said container means may comprise an immunoadsorbent-bound *S. mutans* antigen. Such antigen may be bound to a separate solid-phase immunoadsorbent or directly to the inner walls of a container. A second container may comprise detectably labeled anti-antibody in lyophilized form or in solution.

The carrier may also contain, in addition, a plurality of containers each of which comprises different, predetermined and known amounts of antibody. These latter containers can then be used to prepare a standard curve from which can be interpolated the results obtained from the sample containing the unknown amount of antibody.

In addition, one of ordinary skill in the art would understand that the methods of the invention may be used to identify disease processes caused by or associated with an autoimmune response to or an autoimmune response triggered by antigens from *S. mutans*. While such diseases might be expected to relate to the digestive tract from the teeth to the anus, animal studies have shown that bacterial antigens are able to leave the gut and cause disease in other organs. Thus, the invention herein may have broad applicability beyond the diagnosis of Crohn's disease.

The methods of the invention utilize reagents, procedures, and technologies currently available in virtually all hospital laboratories, such as, for example, immunologic, electrophoretic, and microbiologic techniques. The method of the invention uses methods well known to those skilled in the arts of immunology, microbiology, and medicine, including ELISA, Western Blots, cell culture, immunohistochemistry, SDS-polyacrylamide gel electrophoresis (SDS-PAGE), and biochemical analyses including enzyme activity assay. The above methods may be combined as desired.

The culture, detection and identification of *S. mutans* and its antibodies may be performed using techniques known in the art, for example, as described in U.S. Pat. Nos. 3,746,624; 3,902,969; 4,692,407; 5,334,503; 4,324,782; 4,789,735; 5,281,524; and 4,166,767.

The invention is described in more detail in the following examples, These examples show only a few concrete applications of the invention. It is self evident for one skilled in the art to create several similar applications. Hence the examples should not be interpreted to narrow the scope of the invention, only to clarify the use of the invention.

EXAMPLES

Example 1

Detection of Anti-Antibodies to *S. mutans* in Serum

10 $\mu$l aliquots of serum from patients or controls were added to microcentrifuge tubes containing 10 $\mu$l of *S. pyogenes* cell wall suspension prepared by the method of Stimpson (initially at 20 mg/ml) and 100 $\mu$l of PBS. Aliquots were adsorbed overnight at 4° C. 880 $\mu$l of PBS+2% fetal calf serum (FCS) was then added to each tube and the precipitate was spun out in a microfuge. ELISA assays were then run, initially coating plates with *S. mutans* cell wall suspension prepared by the method of Cromartie, diluted to 40 $\mu$g/ml in PBS. Plates were blocked with 2% FCS in PBS. Samples were applied in final dilutions of 1:200, 1:400, 1:800, 1:1600, and 1:3200 in PBS+2% FCS. Bound antibody was detected with biotinylated anti-human IgG(H&L) diluted to 1:1000 and avidin-peroxidase diluted to 1:4000, and developed with 3,3',5,5'-tetramethylbenzidine stopping the reaction with 0.18 M $H_2SO_4$ and reading at 450 nm. Steps were separated by washings in PBS+0.1% Tween-20. Incubations were 1 hour.

Figure 2:
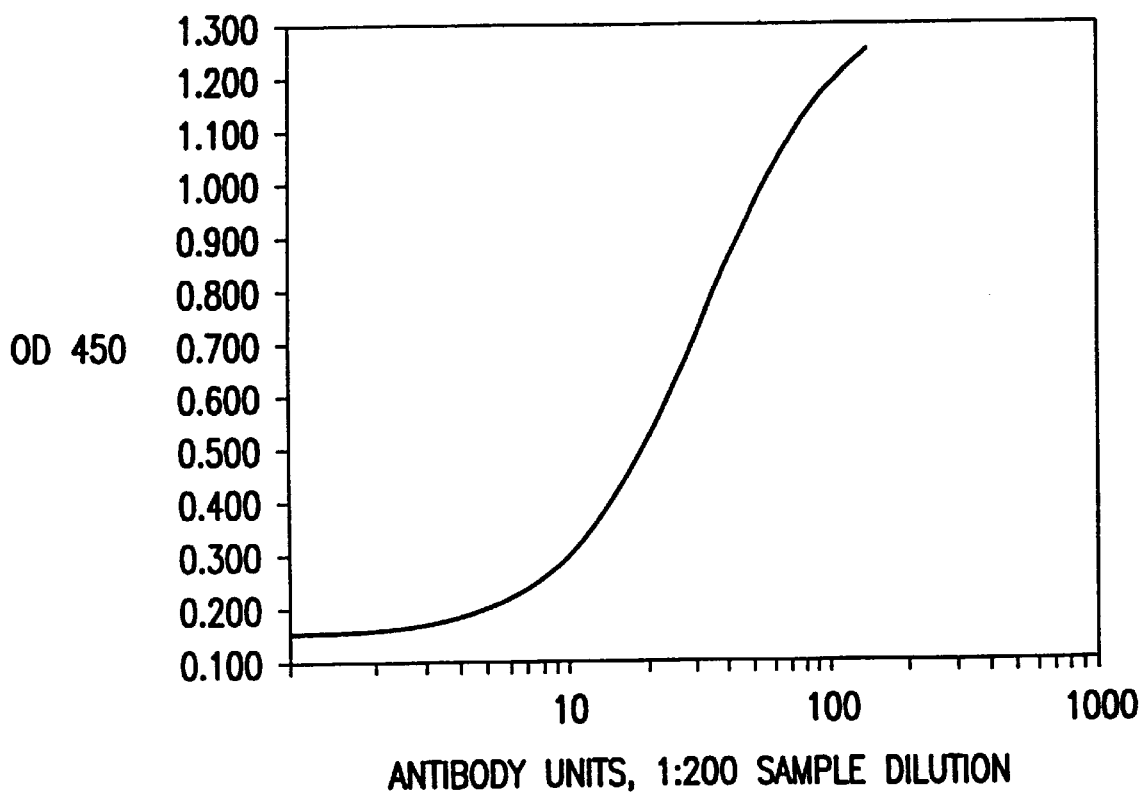
FIG. 2 shows the curve used for interpolation of the data shown in Table 1.

Table 1 shows the results of the assay. Concentration at each dilution was calculated as the mean of 3 values derived from interpolation of OD 450 from a standard curve, with corrections made for dilution factor. Concentration of the sample was calculated as the mean of concentrations measured in several dilutions excluding values from the end of the titration curve. * represents OD 450 values outside the range of the interpolation. The two patients have titers of 44.9 and 100.5 arbitrary units, while the control is negative at 13.9 arbitrary units. FIG. 1 shows the titration curves for the samples used in Example 1. FIG. 2 shows the curve used to determine the titers in Table 1 from the titration curves in FIG. 1.

TABLE 1

| Dilution | Titer | | | Titer Corrected for Dilution | | |
|---|---|---|---|---|---|---|
| | Pt. 1 | Pt. 2 | Control | Pt. 1 | Pt. 2 | Control |
| 200 | 49.5 | 102.5 | 15.4 | 49.5 | 102.5 | 15.4 |
| 400 | 22.6 | 49.8 | 7.1 | 45.1 | 99.6 | 14.2 |
| 800 | 10.0 | 25.0 | 3.0 | 40.2 | 100.1 | 12.0 |
| 1600 | 2.7 | 12.5 | * | 21.9 | 100.2 | * |
| 3200 | * | 6.2 | * | * | 99.9 | * |
| | | | Average Titer: | 44.9 | 100.5 | 13.9 |

Example 2

Cellular Proliferation Induced by *S. Mutans*

40 ml of blood was collected in evacuated, heparinized glass tubes from a patient with Crohn's disease. Blood was diluted with an equal volume of PBS and then layered over Ficoll/Hypaque. After centrifugation, the mononuclear cell fraction found at the interface was harvested by aspiration with a pasteur pipette and was then washed 3 times in PBS and suspended in RPMI as described below at $2\times10^6$ cells per ml and 0.1 ml aliquots were placed in a 96 well plate. *S. mutans* cell wall suspension at 20 mg/ml prepared by the method of Cromartie et al., *J. Exp. Med.* 146:1585–1602 (1977) was diluted serially from 0.1% v/v supplement down to $2\times10^{-6}$% v/v, and 100 µl was added to each well. Mononuclear cells and cell wall suspension were suspended in RPMI-1640 supplemented with 50 µM β-mercaptoethanol (2-ME), 10 mM HEPES, 2 mM L-glutamine, 100 U each Pen/Strep, and 5% FCS. Cells were cultured for 72 hours at 37° C. in room air with 5% $CO_2$. 16 hours before harvesting cells wells were pulsed with 0.5 µCi of tritiated thymidine. Cells were harvested onto glass filter paper discs, which were dried, placed in scintillation fluid and counted in a scintillation counter.

Figure 3:
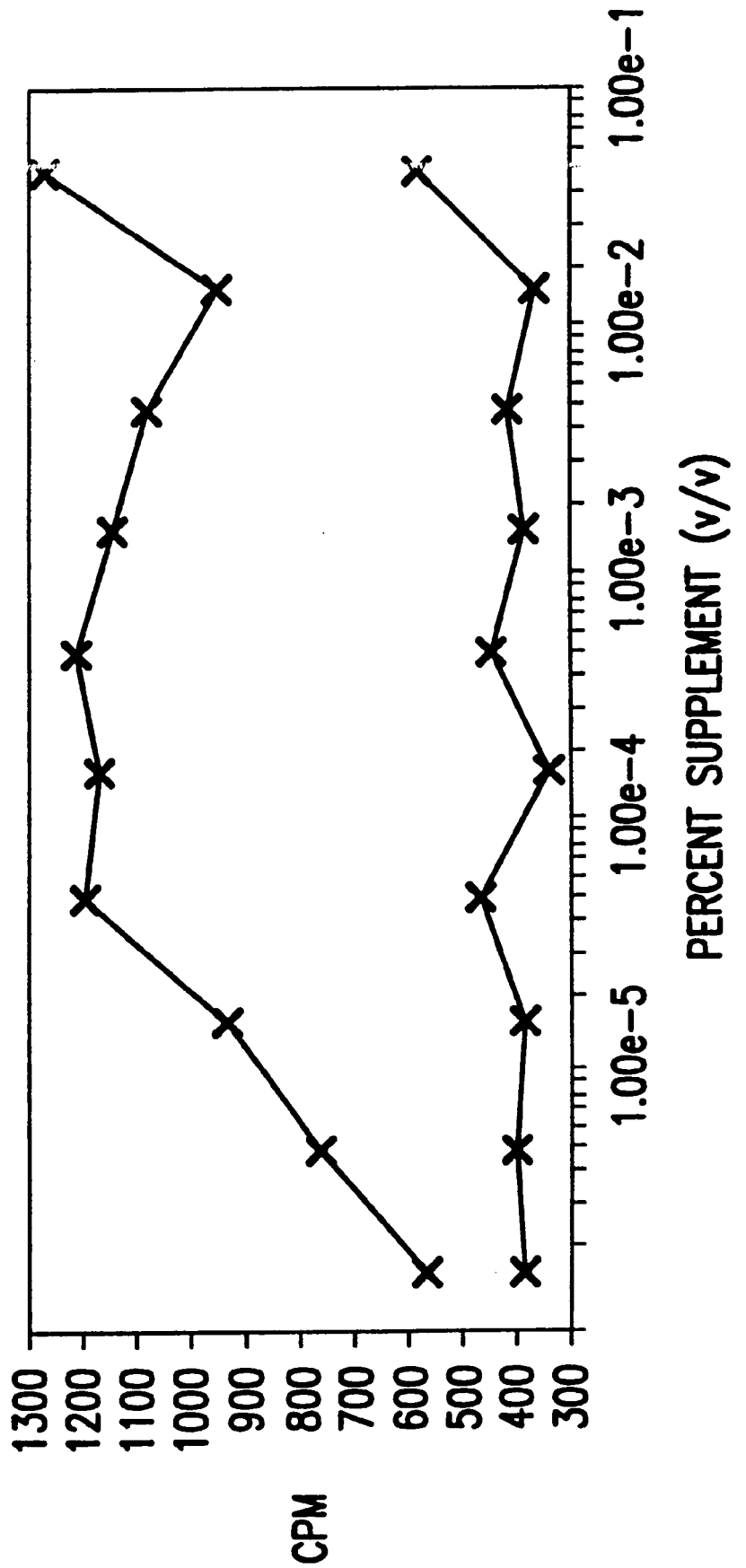
FIG. 3 shows the results of a cellular proliferation assay.

FIG. 3 shows the mild but consistent proliferative response in a patient with Crohn's disease. The lower curve in the figure is the response to bacterial cell supernatant. Control subjects do not have a proliferative response different from the cell supernatant control (data not shown). Proliferative responses to ConA at 5 µg/ml are typically 20000 CPM for both controls and patients.

Example 3
Detection of anti-*S. mutans* antibodies by Western Blot Analysis

20 µl aliquots of *S. mutans* cell wall preparation are treated with sample preparation buffer and run in SDS-PAGE electrophoresis using a 5–10% gradient with a 2.7% crosslinker concentration using Laeminli buffers (Laemmli, U.K., *Nature* 227:680–685 (1970)). After the gel has been run, a Western Blot transfer is performed, and the membrane is blocked with PBS+2% FCS. Strips of the nitrocellulose membrane with *S. mutans* antigens adherent are then incubated in a 1:100 dilution of patient or control serum in PBS+2% BSA. After incubation for 1 hour, strips are washed 4 times and are incubated 1 hour with biotinylated anti-Human IgG diluted to 1:1000 in PBS+2% BSA. Strips are washed 4 times, and are incubated 1 hour with avidin-peroxidase diluted 1:2000. After washing 4 times, strips are immersed in a solution of 4-chloro-1-naphthanol in methanol/Tris-HCl pH 7.6+$H_2O_2$ as described in Hudson.

The pattern of staining on the blot is compared to known Crohn's patients and normal patients, using the pattern of bands to determine whether the patient has Crohn's disease, or whether the disease has exacerbated.

Example 4
Detection of *S. mutans* antigens in Tissue Specimens

Tissue samples are obtained from a patient either at endoscopy, at surgery, or through other procedure. A portion of the tissue is frozen in OCT compound. Sections 4 microns thick are obtained with a refrigerated microtome and are fixed 5 minutes in cold acetone. Sections on the slides are then covered with PBS+10% goat serum for 20 minutes. After removing the PBS+goat serum, anti-*S. mutans* rabbit serum prepared as above diluted in PBS+2%FCS is applied to the slide and incubated for 1 hour. Biotin labeled goat anti-rabbit antibody is then applied in a similar fashion as was the rabbit anti-antibodies to *S. mutans* with a further 1 hour incubation. Avidin-biotin-peroxidase complexes are then formed and applied to the sections as directed using a kit available from Vector Labs. A solution of hydrogen peroxide and 3',3 diaminobenzidine-Na is applied to the slide and allowed to remain for 5–10 minutes. Slides are then stained with 1% Methyl Green in 1% acetic acid for 30 minutes, washed, dried with ethanol, and mounted with Permount. To one skilled in the art, it is obvious that a number of changes could be made in the protocol without changing the essential nature of the protocol. The presence of *S. mutans* antigens, and the relative amount of the same in the tissue is diagnostic of the presence or exaceration of Crohn's disease.

Example 5
Detection of Antibodies to *S. mutans* in Tissue Specimens

Tissue samples are obtained from a patient either at endoscopy, at surgery, or through other procedure. A portion of the tissue is frozen in OCT compound. Sections 4 microns thick are obtained with a refrigerated microtome and are fixed 5 minutes in cold acetone. Sections on the slides are then covered with PBS+10% goat serum for 20 minutes. After the sections have been washed of the PBS+goat serum solution, a solution of antigen or antigens from *S. mutans*, preferably *S. mutans* cell wall preparation as described above, diluted in PBS with or without an additional protein source, preferably 2% BSA, is applied. The solution of antigen or antigens could be any source that provides antigens from or like those from *S. mutans*. After washing with PBS, the slide is sequentially incubated with anti-*S. mutans* antibody, preferably from a rabbit as described above, followed by biotin labeled goat anti-rabbit antibody, avidin-biotin-peroxidase complexes, and development and counterstaining as described in Example 4, with washing between steps with PBS. An optional step before the application of the *S. mutans* antigen or antigens is to perform an incubation with rat anti-*S. mutans* antibody, which will block the binding of detecting antibody to *S. mutans* antigen that may be in the tissue. To one skilled in the art, it is obvious that a number of changes could be made in the protocol without changing the essential nature of the protocol, including the source of the antigen or antigens or their method of preparation. The presence of *S. mutans* antibodies, and the relative amount of the same in the tissue is diagnostic of the presence or exacerbation of Crohn's disease.

Having now fully described the invention, it will be understood by those with skill in the art that the scope may be performed within a wide and equivalent range of conditions, parameters and the like, without affecting the spirit or scope of the invention or any embodiment thereof. All references cited herein are fully incorporated herein by reference.

What is claimed is:

1. A method of diagnosing Crohn's disease in a patient with symptoms of Crohn's disease and suspected of having Crohn's disease, wherein said method comprises
   (A) taking a sample from said patient,
   (B) detecting the presence or absence of antibodies to *S. mutans* in said sample,
   (C) diagnosing Crohn's disease in said patient having said symptoms when said antibodies are detected in said sample.

2. The method of claim 1, wherein said sample is a blood sample.

3. The method of claim 1, wherein said sample is a serum sample.

4. The method of claim 1, wherein said sample is a tissue sample.

5. A method of evaluating whether Crohn's disease has progressed in a patient having symptoms of Crohn's disease and already diagnosed as having Crohn's disease, wherein said method comprises (A) taking a sample from said patient, (B) detecting the presence or absence of antibodies to *S. mutans* in said sample, and (C) evaluating that said Crohn's disease has progressed in said patient having said symptoms when said antibodies are detected in said sample.

6. The method of claim 5, wherein said sample is a blood sample.

7. The method of claim 5, wherein said sample is a serum sample.

8. The method of claim 5, wherein said sample is a tissue sample.

9. The method of any one of claims 1, 2 or 3–8, wherein said patient is an animal patient.

10. The method of any one of claims 1, 2 or 3–8, wherein said patient is a human patient.

* * * * *